United States Patent [19]

Wender et al.

[11] Patent Number: 5,024,661
[45] Date of Patent: Jun. 18, 1991

[54] NON-REUSEABLE HYPODERMIC SYRINGE

[75] Inventors: Harry Wender, Forest Hills; Augusto F. Avila, Long Island City, both of N.Y.

[73] Assignee: Empire Research Corporation, Glendale, N.Y.

[21] Appl. No.: 394,325

[22] Filed: Aug. 16, 1989

[51] Int. Cl.$^5$ .............................................. A61M 5/00
[52] U.S. Cl. ..................................... 604/110; 604/210
[58] Field of Search ............... 604/110, 208, 210, 220, 604/218

[56] References Cited

U.S. PATENT DOCUMENTS

| | | | |
|---|---|---|---|
| 2,502,639 | 4/1950 | Blake | 604/210 |
| 2,707,954 | 5/1955 | Kas, Sr. | 604/210 |
| 4,826,483 | 5/1989 | Molnar, IV | 604/110 |
| 4,840,616 | 6/1989 | Banks | 604/110 |

Primary Examiner—John D. Yasko
Attorney, Agent, or Firm—Darby & Darby

[57] ABSTRACT

A hypodermic syringe is provided which comprises a hollow barrel, a longitudinally slidable and axially rotatable plunger shaft, a sealing means, e.g., a self-resealing rubber cap or sealing gasket, and an integrally-joined cover which includes (i) a charging positioning means for longitudinally moving the shaft within the barrel, (ii) axial rotational means for rotating the shaft of about 180° to a plurality of discharge positions, and (iii) discharging positioning means for longitudinally moving the shaft within the barrel. The hypodermic syringe can only be used once to inject a patient or user with a liquid.

21 Claims, 2 Drawing Sheets

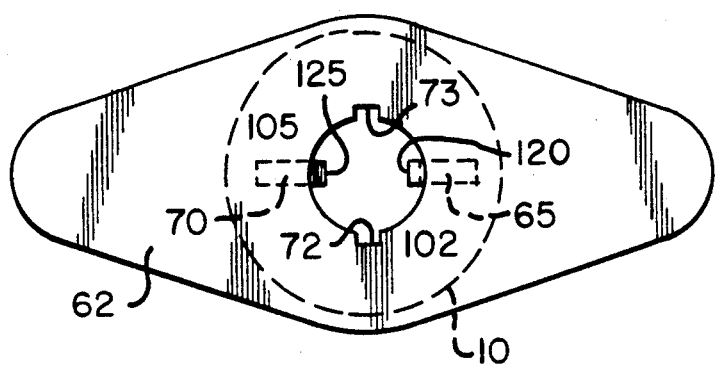
FIG. 3
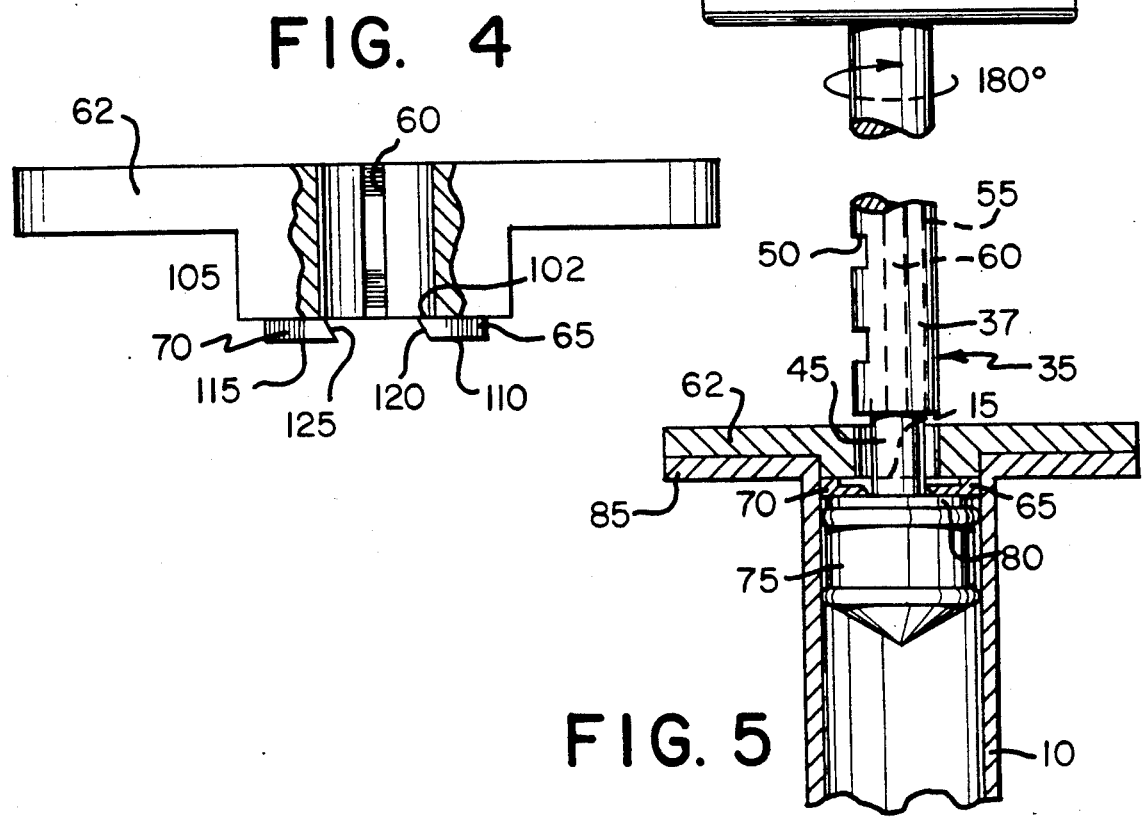
FIG. 4
FIG. 5

NON-REUSEABLE HYPODERMIC SYRINGE

TECHNICAL FIELD

The present invention relates to a medical device, and more particularly to a hypodermic syringe which can only be used only one time to inject a patient or a user with a liquid.

BACKGROUND OF THE ART

The spread of blood- or fluid-borne communicable and contagious diseases, such as Acquired Immune Deficiency Syndrome (AIDS), infectious hepatitis, syphilis and the like, continues to be of grave epidemiological concern. Of particular concern is the spread of AIDS and hepatitis among intravenous (IV) drug-users. It has been broadly estimated that more than half of the incidence of AIDS in an urban population center, e.g., New York City, may be directly attributed to intravenous drug use, i.e., the sharing or exchange of needles among IV drug users.

The incidence of AIDS among IV drug users has become so widespread that public health authorities are advocating the free distribution of clean needles to addict drug users.

It is clearly apparent that a means to limit the use of hypodermic needles to only a single injection in a patient or user would be highly desirable to slow the spread of contagious blood diseases, e.g., AIDS and hepatitis.

DISCLOSURE OF THE INVENTION

The present invention is directed to a hypodermic syringe which, because of its features, can be used for only one injection of liquid, and thereafter the syringe cannot be used again to inject a patient or user.

A principal embodiment of the present invention is directed to a hypodermic syringe comprising (a) a hollow barrel for containing liquid and having a needle hub means, a cover joining means, and a rear open face, said needle hub means adapted to form a holder for a needle to inject liquid from within the barrel through a needle; (b) a longitudinally slidable and axially rotatable plunger shaft having a body, a rear end and a front end, said front end of said shaft positioned within said barrel, said rear end of said shaft positioned outside of said barrel, said rear end of said shaft being adapted to move said shaft longitudinally within the barrel; (c) a cover having an open face and including (i) charging positioning means for longitudinally moving the shaft within the barrel between (I) a first charging position where the front end of the shaft and the needle hub of the barrel are substantially aligned together to (II) a second charging position where the front end of the shaft is longitudinally displaced within the barrel from the needle hub; (ii) axial rotational means for rotating the shaft of about 180° to a plurality of discharge positions when the shaft is in (II) the second charging position; and (iii) discharging positioning means for longitudinally moving the shaft within the barrel where the plurality of discharge positions are selected from the group of positions between a first discharging position where the front end of the shaft and the rear open face of the barrel are substantially aligned to a second position where the front end of the shaft is longitudinally displaced from the rear open face of the barrel, said cover being integrally joined to said cover joining means of said barrel; and (d) a sealing means for preventing the leakage of liquid between the front end of the shaft and the rear open face of said barrel or for preventing the introduction of air into the liquid.

BRIEF DESCRIPTION OF THE DRAWINGS

The foregoing and other features of the present invention will be more readily apparent from the following detailed description and drawings of illustrative embodiments of the invention in which

FIG. 3 is a top view of the cover of the hypodermic syringe.

FIG. 4 is a front view of the top cover of the hypodermic syringe.

FIG. 5 is a sectional view showing the hypodermic syringe of FIG. 1 "charged" or filled with liquid prior to injection into a patient.

DESCRIPTION OF THE PREFERRED EMBODIMENTS

Figure 1:
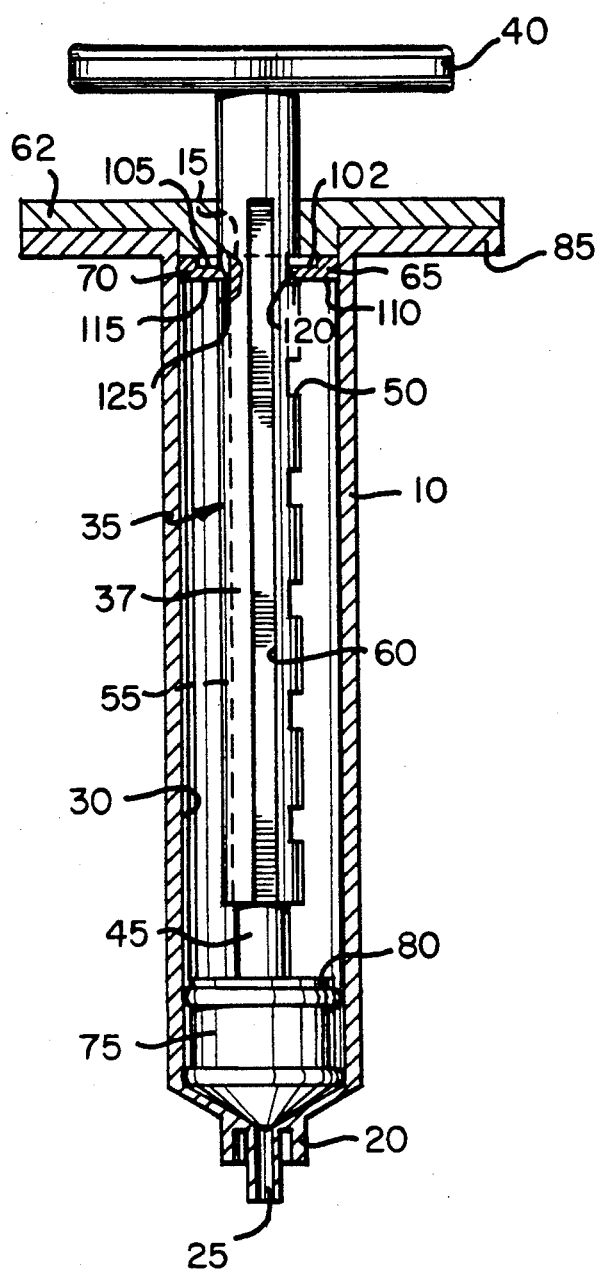
FIG. 1 is a sectional view showing the hypodermic syringe of the present invention prior to use, i.e., prior to "charging" or filling the syringe barrel with liquid.

As shown in FIG. 1, the hypodermic syringe of the present invention has as a first component a hollow barrel 10 for containing liquid and having a rear open face 15, a flanged surface 85, and a needle hub 20. The needle hub 20 is adapted into an injection port 25 and is also adapted to form a holder for a needle (not shown) to inject liquid from within the barrel 10 through the needle. The hollow barrel 10 further comprises an inner barrel wall 30.

The hypodermic syringe has as a second component a longitudinally moveable (slidable) and axially rotatable plunger shaft 35 extending partially through the hollow barrel 10. The plunger shaft 35 has a body 37, a rear end 40 and a front end 45. The rear end 40 is positioned outside of the barrel and is adaptable to move the shaft 35 longitudinally within the barrel 10. The front end 45 is positioned within the inner barrel wall 30 and is further adapted to attach a sealing gasket (self re-sealing rubber cap) 75 for preventing the leakage of liquid between the shaft and out the rear open face of the barrel. A support stopper 80 is also shown in FIG. 1 and secures the attachment of the sealing gasket 75 to the front end 45 of the shaft.

As also shown in FIG. 1, the plunger shaft 35 additionally comprises at least one locking groove 50 which is positioned on the body 37 of the shaft 35. The plunger shaft 35 additionally comprises a longitudinal slot 55. In other embodiments a longitudinal guide 60 is provided on the body 37 of the shaft 35.

The hypodermic syringe has as a third component a cover 62 having an open surface and integrally joined to the flanged surface 85 of the barrel 10.

The cover 62 may be integrally joined to the flanged surface 85 of the barrel 10 using methods well known to those skilled in the art. A preferred method of joining the cover to the flanged surface of the barrel uses an energy director and is called ultrasonic welding. An apparatus used for that purpose is referred to as an ultrasonic welding machine and is available from Bronson (Hartford, CT).

As shown in FIG. 1, there are two members positioned directly across from each other on the cover 62 for longitudinally moving the plunger shaft 35 within the barrel 10, and by consequence, charging or discharging of liquid within the barrel 10 through the injection port 25. The charging releasing member 65 longitudinally moves the plunger shaft 35 within the hollow barrel 10 between (I) a first charging position where the front end of the shaft and the needle hub of the barrel are substantially aligned together to (II) a second charging position where the front end 45 of the plunger shaft 35 is longitudinally displaced within the barrel from the needle hub 20 and injection port 25. The discharging releasing member 70 longitudinally moves the plunger shaft 35 within the hollow barrel 10 between a first position where the front end 45 of the shaft 35 and the needle hub 20 of the barrel 10 are substantially aligned to a second position where the front end 45 is longitudinally displaced from the rear open face 15 of the hollow barrel 10.

As shown in FIG. 1, the charging release member 65 is aligned with the locking grooves 50 and the discharging release member 70 is aligned with the longitudinal slot 55. As also shown in FIG. 1, the charging release member 65 and the discharging release member 70 each includes an outer surface 102 and 105, respectively, and an inner surface, 110 and 115, respectively.

In FIG. 1, the charging release member 65 is attached to the cover 62 proximate to the rear open face 15 of the barrel. The discharging release member 70 is also attached to the cover 62 and is 180° across the cover opening from the charging release member 70.

The charging release member 65 is adapted to provide a unidirectionally flexible point 120 which will longitudinally move the plunger shaft 35 within the hollow barrel 10 between (I) a first charging position where the front end of the shaft 35 and the needle hub 20 of the barrel 10 are substantially aligned together to (II) a second charging position where the front end of the shaft 45 is longitudinally displaced within the barrel from the needle hub 20 and injection port 25 when the locking groove or grooves 50 are aligned with the charging release member 65. When any of the locking grooves 50 move past the unidirectionally flexible point 120 as the front end 45 of the plunger shaft 35 is longitudinally displaced from the needle hub 20 and injection port 25, the return (or reverse movement) of the locking grooves 50 past the unidirectionally flexible point 120 of the charging release member 65 and of the longitudinal displacement of the front end 45 of the plunger shaft from the rear open face 15 of the hollow barrel 10 will be prevented.

The discharging release member 70 is also adapted to provide a unidirectionally flexible point 125. As shown in FIG. 1, the longitudinal slot 55 is substantially aligned with the discharging release member 70. In such an alignment, there is no obstruction of longitudinal movement vis-a-vis the longitudinal slot 55 and the discharging release member 70.

The longitudinal guide 60 rotates the plunger shaft 35 of about 180° to a plurality of discharge positions when the shaft is in (II) the second charging position. The (II) second charging position has been reached where the front end 45 of the shaft 35 cannot be further longitudinally displaced within the barrel 10 from the needle hub 20. In a preferred embodiment, the longitudinal guide 60 is positioned midway between the locking grooves 50 and the longitudinal slot 55 as shown in FIG. 2.

Figure 2:
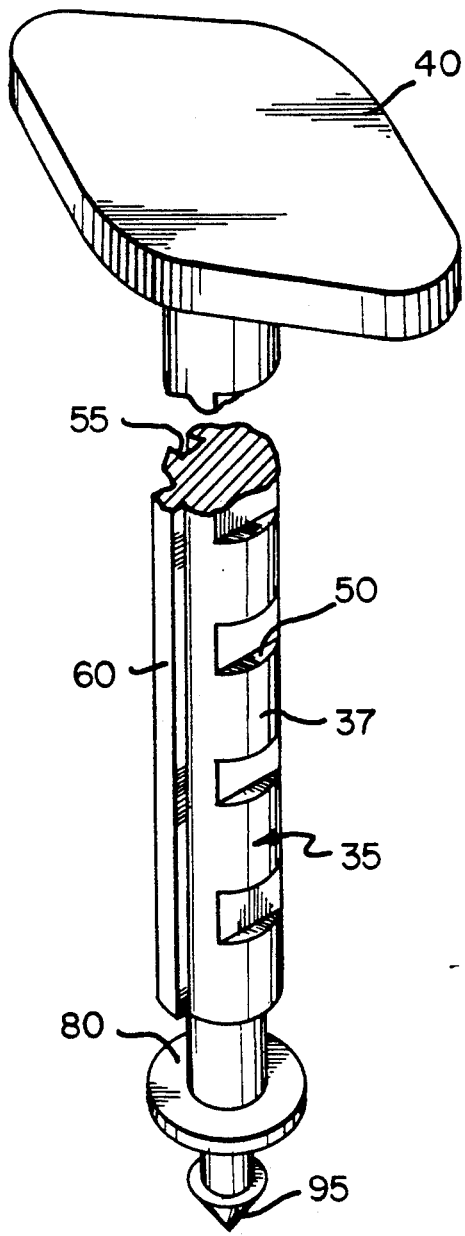
FIG. 2 is a perspective cutaway view of the plunger shaft removed from the barrel of the hypodermic syringe.

In FIG. 2, there is provided a perspective cutaway view of the plunger shaft 35 removed or isolated from the hollow barrel 10 of the hypodermic syringe. This perspective shows the plunger shaft 35, the body 37, rear end 40 of the shaft, locking grooves 50, longitudinal guide 60, conical end marker 95 with support stopper 80 for the sealing gasket (not shown).

FIG. 3 is a top view of the cover 62 of the hypodermic syringe of the present invention. The charging release member 65 and discharging release member 70 are shown in FIG. 3 positioned diametrically across from each other on the cover 62. Also shown are a first guide notch 72 and a second guide notch 73 also positioned diametrically across from each other on the cover 62 and each approximately midway between the charging release member 65 and the discharging release member 70. Each guide notch 72 and 73 is adapted to secure the longitudinal guide 60 in place before or after axial rotation of the plunger shaft 35. The first guide notch 72 is adapted to secure the longitudinal guide 60 in place when the hypodermic syringe is being charged from (I) a first charging position to (II) a second charging position. After the shaft has been axially rotated 180°, as shown in FIG. 5, the second guide notch 73 secures the longitudinal guide 60 in place. The dotted line shown in FIG. 3 represents the outline of the hollow barrel 10 to which the cover 62 is integrally joined according to the present invention.

FIG. 4 is a front view of the top cover 62 of the hypodermic syringe of the present invention. In FIG. 4 is shown the charging release member 65 and discharging release member 70. Also shown are the unidirectionally flexible points, 120 and 125, of the respective release members, 65 and 70. In addition, the longitudinal guide 60 of the plunger shaft is shown in FIG. 4.

FIG. 5 is a sectional view showing the hypodermic syringe of FIG. 1 after it is charged with liquid prior to injection into a patient.

The plunger shaft 35 has been axially rotated 180° in FIG. 5 so that the locking grooves 50 are substantially aligned with the discharging release member 70 and the longitudinal slot 55 is substantially aligned with the charging release member 65. From the position as shown in FIG. 5, the plunger shaft 35 may be longitudinally moved within the hollow barrel 10 so that the front end 45 of the plunger shaft is longitudinally displaced from the rear open face 15 of the hollow barrel. As the plunger shaft 35 moves longitudinally within the hollow barrel 10 by the longitudinal displacement of the front end 45 from the rear open face 15, liquid is pushed through the injection port 25 and any needle placed over the needle hub 20.

While the invention has been particularly shown and described with reference to preferred embodiments thereof, it will be understood by those skilled in the art that various changes in form and details may be made therein without departing from the spirit and scope of the invention.

What is claimed is:

1. A hypodermic syringe for single usage, comprising:
   a hollow barrel for containing liquid, said barrel having a needle hub for engaging a needle at a front end and having a rear end with an open face, and cover joining means proximate said open face, said barrel having a longitudinal axis;
   a plunger shaft within said barrel, said shaft including a rear end, front end and body therebetween, said shaft being adapted to move longitudinally in said barrel when a force is applied thereto;

a cover connected to said cover joining means, said cover having an opening, said rear end of said shaft extending through said opening to be external of said barrel;

first means and second means for engaging said shaft, said first and second engagement means having fixed attachment in relation to said barrel;

third engagement means fixed on said shaft between said shaft ends, said first engagement means when engaged with said third engagement means permitting longitudinal sliding motion of said shaft only away from said needle hub, said second engagement means when engaged with said third engagement means permitting longitudinal sliding motions of said shaft only toward said needle hub, at a given time not more than one of said first and second engagement means being able to engage said third engagement means;

means for releasing said third engagement means simultaneously from said first and second engagement means only when said shaft is withdrawn from said hub, said shaft when released being rotatable about said longitudinal barrel axis from a first angular position where said third engagement means is subject to engagement with said first engagement means to a second angular position where said third engagement means is subject to engagement with said second engagement means, said shaft being subject to withdrawal from said needle hub only one time.

2. A hypodermic syringe as in claim 1, wherein the shaft further includes a longitudinal slot.

3. A hypodermic syringe as in claim 2, wherein the shaft further includes a longitudinal guide positioned between said locking grooves and said longitudinal slot.

4. A hypodermic syringe as in claim 1, wherein the front end of the shaft further includes a conical end member for attaching sealing means for preventing leakage.

5. A hypodermic syringe as in claim 4, wherein the front end of the shaft further comprises a support stopper proximate to the conical end member for attaching said sealing means.

6. A hypodermic syringe as in claim 5, wherein said sealing means comprises a self-resealing rubber cap or sealing gasket.

7. A hypodermic syringe as in claim 1, wherein said first engagement means comprises a charging release member, said member having an outer surface and an inner surface.

8. A hypodermic syringe as in claim 7, wherein the charging release member further comprises a unidirectionally flexible point permitting movement of the shaft longitudinally within the barrel so that the front end of the shaft is longitudinally displaced from the needle hub of the barrel.

9. A hypodermic syringe as in claim 1, wherein the cover comprises a first guide notch and a second guide notch, said first and second guide notches being positioned opposite to each other on said cover.

10. A hypodermic syringe as in claim 2 and further comprising a longitudinal guide on said shaft, and, wherein the cover comprises a first guide notch and a second guide notch, said first and second guide notches being adapted to the shape of the longitudinal guide and being positioned opposite to each other on said cover.

11. A hypodermic syringe as in claim 1, wherein said second engagement means includes a discharging release member, said discharging release member having an outer surface and an inner surface.

12. A hypodermic syringe as in claim 11, wherein the discharging release member further comprises a unidirectionally flexible point permitting movement of the shaft longitudinally within the barrel so that the front end of the shaft is longitudinally displaced from the rear open face of the barrel.

13. A hypodermic syringe as in claim 1, wherein said cover is integrally joined to said cover joining means by ultrasonic welding.

14. A hypodermic syringe as in claim 1, wherein said third engagement means includes at least one locking groove on the body of said shaft.

15. A hypodermic syringe as in claim 1, wherein said third engagement means includes a plurality of locking grooves on the body of said shaft.

16. A hypodermic syringe as in claim 1, wherein said first and second engaging means are connected to said cover.

17. A hypodermic syringe as in claim 7, and further comprising at least one locking groove on said shaft body, said charging release member making ratchet-like engagement with said at least one groove to permit said unidirectional longitudinal motion away from said needle hub.

18. A hypodermic syringe as in claim 11, and further comprising at least one groove on said shaft body, said discharging release member making ratchet-like engagement with said at least one groove to permit said unidirectional longitudinal motion toward said needle hub.

19. A hypodermic syringe comprising:

a hollow barrel for containing a liquid and having a needle hub, a cover joining means, and a rear open face, said needle hub being adapted to hold a needle for discharging liquid from within the barrel through said needle;

a longitudinal slidable and axially rotatable plunger shaft having a body, a rear end and a front end, said front end of said shaft positioned within said barrel, said rear end of said shaft positioned outside of said barrel, said rear end of said shaft being adapted to move said shaft longitudinally within the barrel;

a cover having an open face and including (i) charging positioning means for longitudinally moving the shaft within the barrel between a first charging position where the front end of the shaft and the needle hub are substantially aligned together to a second charging position where the front end of the shaft is longitudinally displaced within the barrel from the needle hub, (ii) axial rotational means for rotating the shaft about 180° to a plurality of discharge positions when the shaft is in the second charging position; and (iii) discharging positioning means for longitudinally moving the shaft within the barrel where the plurality of discharge positions are selected from the group of positions between a first discharging position, where the front end of the shaft and the rear open face of the barrel are substantially aligned to a second discharging position where the front end of the shaft is longitudinally displaced from the rear open face of the barrel, said cover being integrally joined to said cover joining means of said barrel; and a sealing means for preventing the leakage of liquid between the front end of said shaft and out of the rear open face of said barrel or the introduction of air into the liquid;

said shaft further including at least one locking groove on the body of said shaft;

20. A hypodermic syringe comprising:

a hollow barrel for containing a liquid and having a needle hub, a cover joining means, and a rear open face, said needle hub being adapted to hold a needle for discharging said liquid from within the barrel through said needle;

a longitudinally slidable and axially rotatable plunger shaft having a body, a rear end and a front end, said front end of said shaft positioned within said barrel, said rear end of said shaft positioned outside of said barrel, said rear end of said shaft being adapted to move said shaft longitudinally within the barrel;

a cover having an open face and including (i) charging positioning means for longitudinally moving the shaft within the barrel between a first charging position where the front end of the shaft and the needle hub of the barrel are substantially aligned together to a second charging position where the front end of the shaft is longitudinally displaced within the barrel from the needle hub, (ii) means for axially rotating the shaft about 180° to a plurality of discharge positions when the shaft is in the second charging position; and (iii) discharging positioning means for longitudinally moving the shaft within the barrel where the plurality of discharge positions are selected from the group of positions between a first discharging position where the front end of the shaft and the rear open face of the barrel are substantially aligned to a second discharging position where the front end of the shaft is longitudinally displaced from the rear open face of the barrel, said cover being integrally joined to said cover joining means of said barrel; and a sealing means for preventing the leakage of liquid between the front end of said shaft and out of the rear open face of said barrel or the introduction of air into the liquid;

said charging positioning means for longitudinally moving the shaft within the barrel comprises a charging release member, said member having an outer surface and an inner surface, said charging release member further having a unidirectionally flexible point permitting movement of the shaft longitudinally within the barrel so that the front end of the shaft is longitudinally displaced from the needle hub of the barrel.

21. A hypodermic syringe comprising:

a hollow barrel for containing a liquid and having a needle hub, a cover joining means, and a rear open face, said needle hub being adapted to hold a needle for discharging liquid from within the barrel through said needle;

a longitudinally slidable and axially rotatable plunger shaft having a body, a rear end and a front end, said front end of said shaft positioned within said barrel, said rear end of said shaft positioned outside of said barrel, said rear end of said shaft being adapted to move said shaft longitudinally within the barrel;

a cover having an open face and including (i) charging positioning means for longitudinally moving the shaft within the barrel between a first charging position where the front end of the shaft and the needle hub are substantially aligned together to a second charging position where the front end of the shaft is longitudinally displaced within the barrel from the needle hub, (ii) axial rotational means for rotating the shaft about 180° to a plurality of discharge positions when the shaft is in the second charging position; and (iii) discharging positioning means for longitudinally moving the shaft within the barrel where the plurality of discharge positions are selected from the group of positions between a first discharging position where the front end of the shaft and the rear open face of the barrel are substantially aligned to a second discharging position where the front end of the shaft is longitudinally displaced from the rear open face of the barrel, said cover being integrally joined to said cover joining means of said barrel;

a sealing means for preventing the leakage of liquid between the front end of said shaft and out the rear open face of said barrel or the introduction of air into the liquid;

said charging positioning means for longitudinally moving the shaft within the barrel comprising a discharging release member, said member having an outer surface and an inner surface, and said discharging release member further comprises a unidirectionally flexible point permitting movement of the shaft longitudinally within the barrel so that the front end of the shaft is longitudinally displaced from the rear open face of the barrel.

* * * * *